(12) United States Patent
Chu et al.

(10) Patent No.: US 7,615,542 B2
(45) Date of Patent: Nov. 10, 2009

(54) DIOXOLANE THYMINE AND COMBINATIONS FOR USE AGAINST 3TC/AZT RESISTANT STRAINS OF HIV

(75) Inventors: Chung K. Chu, Athens, GA (US); Raymond F. Schinazi, Atlanta, GA (US)

(73) Assignees: University of Georgia Research Foundation, Inc., Athens, GA (US); Emory UNiversity, Athens, GA (US)

( * ) Notice: Subject to any disclaimer, the term of this patent is extended or adjusted under 35 U.S.C. 154(b) by 0 days.

(21) Appl. No.: 10/530,088

(22) PCT Filed: Dec. 8, 2003

(86) PCT No.: PCT/US03/39029

§ 371 (c)(1),
(2), (4) Date: Apr. 1, 2005

(87) PCT Pub. No.: WO2004/052296

PCT Pub. Date: Jun. 24, 2004

(65) Prior Publication Data

US 2005/0209196 A1    Sep. 22, 2005

Related U.S. Application Data

(60) Provisional application No. 60/431,812, filed on Dec. 9, 2002.

(51) Int. Cl.
*A61K 31/7072* (2006.01)
*A61K 31/51* (2006.01)
*C07H 19/06* (2006.01)
*C07H 19/10* (2006.01)
*C07F 9/09* (2006.01)
*C07D 239/22* (2006.01)

(52) U.S. Cl. .......................... 514/50; 514/51; 514/274; 536/28.54; 544/243; 544/314

(58) Field of Classification Search .................. 514/274
See application file for complete search history.

(56) References Cited

U.S. PATENT DOCUMENTS

| | | | |
|---|---|---|---|
| 5,041,449 A | 8/1991 | Belleau et al. | |
| 5,047,407 A | 9/1991 | Belleau et al. | |
| 5,270,315 A | 12/1993 | Belleau et al. | |
| 5,276,151 A | 1/1994 | Liotta | |
| 5,852,027 A | 12/1998 | Liotta et al. | |
| 6,350,753 B1 | 2/2002 | Belleau et al. | |
| 6,855,821 B2 | 2/2005 | Du et al. | |
| 7,119,202 B1 | 10/2006 | Belleau et al. | |

OTHER PUBLICATIONS

The Merck Manual of Diagnosis and Therapy, Seventeenth Edition, published by Merck Research Laboratories, (1999), edited by Beers and Berkow, pp. 1312-1323.*

The Merck Manual of Diagnosis and Therapy, Seventeenth Edition, published 1999 by Merch Research Laboratories, Ed. by Beers and Berkow, pp. 1132-1135.*
Kim et al., "Asymmetric Synthesis of 1,3-Dioxolane-Pyrimidine Nucleosides and Their Anti-HIV Activity" Journal of Medicinal Chemistry (1992) vol. 35, pp. 1987-1995.*
Chu et al., *J. Org. Chem.* 1991, 56(23):6503-6505.
Choi et al, *J. Am. Chem. Soc.* 1991, 113:9377-9379.
Belen'kii, M.S. et al. "Multiple drug effect analysis with confidence interval" *Antiviral Research* 25:1-11 (1994).

(Continued)

*Primary Examiner*—Shaojia Anna Jiang
*Assistant Examiner*—Eric S Olson
(74) *Attorney, Agent, or Firm*—Henry D. Coleman; R. Neil Sudol; William J. Sapone

(57) ABSTRACT

The present invention relates to the use of a dioxolane thymine compound according to the chemical structure of Formula (I): where $R^1$ is H, an acyl group, a $C_1$-$C_{20}$ alkyl or ether group, a phosphate, diphosphate, triphosphate or phosphodiester group, for use in the treatment of HIV infections which exhibit resistance to 3TC and/or AZT. Preferably, compounds according to the present invention are combined with at least one anti-HIV agent which inhibits HIV by a mechanism other than through the inhibition of thymidine kinase (TK). These agents include those selected from among nuleocoside reverse transcriptase inhibitors (NRTI), non-nucleoeoside reverse transcriptase inhibitors, protease inhibitors, fusion inhibitors, among others. These agents are generally selected from the group consisting of 3TC (Lamivudine), AZT (Zidovudine), (–)-FTC, ddI (Didanosine), ddC (zalcitabine), abacavir (ABC), tenofovir (PMPA), D-D4FC (Reverset), D4T (Stavudine), Racivir, L-D4FC, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fuseon and mixtures thereof. The TK dependent agents, such as AZT and D4T, may be used in combination with one of the dioloxane thymine compounds according to the present invention, but the use of such agents may be less preferred. In preferred compositions according to the present invention, $R^1$ is preferably H or a $C_2$-$C_{18}$ acyl group or a monophosphate group. Pharmaceutical compositions and methods of reducing the likelihood that a patient at risk for contract an HIV infection will contract the infection are other aspects of the present invention.

(I)

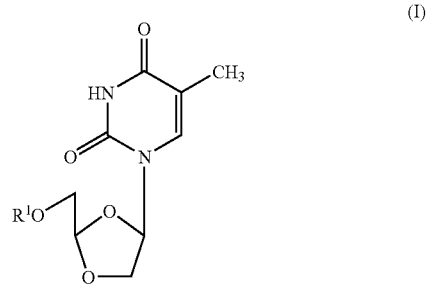

16 Claims, No Drawings

OTHER PUBLICATIONS

Buckheit, Jr., R.W. et al. "Characterization of an HIV-1 Isolate Displaying an Apparent Absence of Virion-Associated Reverse Transcriptase Activity" *AIDS Research and Human Retroviruses* 7:295-302 (1991).

Chu, C.K. et al. "Asymmetric Synthesis of Enantiomerically Pure (-)-(1'R,4'R)-Dioxolane-thymine and Its Anti-HIV Activity." *Tetrahedron Letters* 32:3791-3794.

* cited by examiner

DIOXOLANE THYMINE AND COMBINATIONS FOR USE AGAINST 3TC/AZT RESISTANT STRAINS OF HIV

RELATED APPLICATIONS

This application claims the benefit of priority of provisional application No. 60/431,812, filed Dec. 9, 2002.

STATEMENT OF GOVERNMENTS RIGHTS

This invention was made with government support under a grant from the National Institutes of Health, Grant No. AI32351. The U.S. Government has certain rights in this invention.

FIELD OF THE INVENTION

The present invention relates to pharmaceutical compositions and methods for the treatment of HIV infections which are resistant to treatment with 3TC and/or AZT.

BACKGROUND OF THE INVENTION

Since the discovery of AZT and 3TC as potent inhibitors of human immunodeficiency virus, a number of other nucleoside analogs such as FTC (emtricitabine), DAPD (andoxavir), 3TC (lamivudine or epivir), DDI (didanosine), DDC, D4T (stavudine), 2'-ara-fluoro-DDC, as well as numerous other agents have been synthesized and tested for use against HIV.

HIV is a prototype for pathogenic retroviruses, i.e., viruses that use reverse transcription to replicate. Reverse transcription mechanisms are required by those viruses having an RNA genome wherein the RNA is copied by a polymerase into DNA for subsequent replication. Certain DNA viruses use, in part, reverse transcription mechanisms to replicate such as, for example, hepatitis B virus. Reverse transcriptase is the virally-encoded polymerase used by retroviruses for this purpose.

Two nucleoside analogue reverse transcriptase (RT) inhibitors in combination with a potent protease inhibitor (e.g., nelfinavir) or a non-nucleoside RT inhibitor (e.g., sustiva) are generally recommended to achieve suppression of viral replication in current treatment protocols for HIV-1 infected individuals. Nucleoside analogue reverse transcriptase inhibitors in current use are described hereinbelow.

3'-Azido-3'-deoxythymidine (AZT, zidovudine) is administered at a dosage of 600 mg orally daily in two divided doses. The major dose-limiting toxicity of AZT is on bone marrow. Clinical trials demonstrate that therapy delays clinical evidence of disease progression in previously untreated persons with CD4+T cell counts below 500 cells/mm$^3$. AZT is generally not used as a single agent.

Dideoxyinosine (ddI, didanosine) is administered orally as an inosine prodrug and is formulated with a buffer directed at gastric acid because of the acid lability of dideoxyadenosine. The major toxicities associated with ddI are pancreatitis and peripheral neuropathy. ddI was demonstrated to be equal or superior to AZT in antiviral and immunomodulatory effects and to provide additional clinical benefits to patients who have used AZT.

Dideoxycytosine (ddC) is a nucleoside analogue reverse transcriptase inhibitor that exhibits potent antiretroviral activity in vitro. Dose escalation of ddC is limited by peripheral neuropathy, however, and ddC is therefore used only in combination regimens or for the treatment of patients who are intolerant of, or unresponsive to, other antiretrovirals. ddC is administered at a dosage of 0.75 mg three times daily and has been used extensively in combination regimens for persons with advanced AIDS who are intolerant of other antiretroviral chemotherapeutic agents.

D4T (stavudine), a thymidine analogue, has been investigated in patients with moderate to advanced HIV-1 infection, especially those with previous AZT experience. However, peripheral neuropathy is a major side effect.

Lamivudine (3TC) is well tolerated and results in acute reductions in plasma HIV-1 RNA levels. However, a single mutation in reverse transcriptase at position 184 results in a 100-fold to 1,000-fold decrease in susceptibility to lamivudine. Any measurable degree of viral replication in the presence of the drug results in the rapid emergence of resistant mutations. Lamivudine is associated with suppression of the erythroid and myeloid elements of bone marrow. Lamivudine and AZT are being widely used as a combination with a protease inhibitor. The common resistant mutations observed after 3TC treatment are the M184V or M184I in the HIV-RT gene.

Abacavir is usually given as 600 mg, orally, daily in 2 divided doses. The drug is compromised by mutations in the reserve transcriptase (RT) gene. The efficacy of abacavir is compromised by the emergence of reverse transcriptase drug-resistant viral variants. In vitro studies have shown that the single mutations 65R, 74V, 184V, and 115F in the RT gene confer 2-3-3 fold decreases in susceptibility to abacavir. Mutants harboring 2 or 3 of these mutations exhibit approximately 10-fold resistance to the drug. In clinical studies, patients with more than 2 RT mutations showed a markedly inferior response to abacavir.

Tenofovir (lodenosine) is a fluoridated compound with similar structure and activity to ddI. Unlike ddI, stomach acids do not degrade F-ddA, so it can be administered without an antacid, thereby avoiding side effects attributable to the use of a buffer. Resistance to F-ddA is slow to emerge and the drug has shown in vitro activity against strains of HIV resistant to AZT, ddI, and ddC.

In light of rapid rates of viral replication, the highly error-prone HIV-1 reverse transcriptase, and the inability of currently available antiretroviral agents to completely inhibit HIV-1 replication, the development of resistance to antiretroviral drugs has been an inevitable consequence of drug exposure. Viral variants resistant to all antiretroviral agents in active use have been demonstrated.

The present anti-HIV protocols focus primarily on the interruption of the virus replication cycle, through the inhibition of viral enzymes involved in viral replication. Though this has resulted in some control of the virus, over one-fourth of treatment naive individuals are infected with a virus with reduced susceptibility to one or more of the currently FDA-approved drugs. Moreover, up to 3% of newly diagnosed individuals are infected with a virus that is resistant to drugs in all types of currently approved therapies.

Retroviral, especially HIV, therapy is now thought to be a life-long process. Therefore, it is crucial to develop effective treatments that can be successfully administered for long periods of time for the suppression of retroviruses, and in particular, the prevention and/or inhibition of HIV, especially those strains of HIV which have become resistant to more traditional therapies.

(−)-(1'R,4'R)-Dioxolane-thymine is a potential anti-HIV agent which has shown significant anti-HIV activity. See, C. K. Chu, et al., *Tetrahedron Letters*, Vol. 32, No. 31, pp. 3791-3794 (1994). This nucleoside analog has never been utilized clinically because its anti-HIV activity alone has not been considered potent enough to be a viable, clinically useful anti-HIV agent.

BRIEF DESCRIPTION OF THE INVENTION

The present invention relates to the use of a dioxolane thymine compound according to the chemical structure:

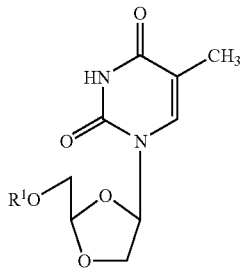

where $R^1$ is H, an acyl group, a $C_1$-$C_{20}$ alkyl or ether group, a phosphate, diphosphate, triphosphate or phosphodiester group, for use in the treatment of HIV infections which exhibit resistance to 3TC and/or AZT. Preferably, compounds according to the present invention are combined with at least one anti-HIV agent which inhibits HIV by a mechanism other than through the inhibition of thymidine kinase (TK). These agents include those selected from among nucleoside reverse transcriptase inhibitors (NRTI), non-nucloeoside reverse transcriptase inhibitors, protease inhibitors, fusion inhibitors, among others. These agents are generally selected from the group consisting of 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-D4FC, NVP (Nevirapine), DLV (Delavirdine), EFV (Efavirenz, Sustiva), SQVM (Saquinavir mesylate), RTV (Ritonavir), IDV (Indinavir), SQV (Saquinavir), NFV (Nelfinavir), APV (Amprenavir), LPV (Lopinavir, kaletra), enfuvirtide (fuseon) and mixtures thereof. The TK dependent agents, such as AZT and D4T, may be used in combination with one of the dioloxane thymine compounds according to the present invention, but the use of such agents may be less preferred. In preferred compositions according to the present invention, R is preferably H or a $C_2$-$C_{18}$ acyl group or a monophosphate group.

Compositions according to the present invention comprise an effective amount of at least one dioxolane thymine compound according to the present invention in combination with at least one additional anti-HIV agent which acts to inhibit HIV by a mechanism other than through the inhition of HIV thymidine kinase enzyme. Such anti-HIV agents are preferably selected from the group consisting of nucleoside reverse transcriptase inhibitors (NRTI), non-nucloeoside reverse transcriptase inhibitors, protease inhibitors, fusion inhibitors, among others. Exemplary agents which may be used in this aspect of the present invention are selected from the group consisting of (−)-FTC, ddI (Didanosine), ddC (zalcitabine), abacavir (ABC), tenofovir (MPA), D-D4FC (Reverset), D4T (Stavudine), Racivir, L-D4FC, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir) and mixtures thereof. Certain TK dependent agents, such as AZT and D4T, also may be used in combination with one of the dioxolane thymine compounds according to the present invention.

In another aspect of the present invention, pharmaceutical compositions comprise an effective amount of at least one dioxolane thymine compound as set forth above in combination with an effective amount of at least one additional anti-HIV agent which inhibits the growth, replication or elaboration of HIV through a mechanism other than by inhibiting thymidine kinase, optionally in combination with a pharmaceutically acceptable carrier, additive or excipient. These additional anti-HIV agents are generally selected from the group consisting of nucleoside reverse transcriptase inhibitors (NRTI), non-nucloeoside reverse transcriptase inhibitors, protease inhibitors, fusion inhibitors, among others. Exemplary agents which may be used in this aspect of the present invention are selected from the group consisting of (−)-FTC, ddI (Didanosine), ddC (zalcitabine), abacavir (ABC), tenofovir (PMPA), D-D4FC (Reverset), Racivir, L-D4FC, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir) and mixtures thereof. Certain TK dependent agents, such as AZT and D4T, also may be used in combination with one of the dioxolane thymine compounds according to the present invention.

DETAILED DESCRIPTION OF THE INVENTION

The following definitions will be used throughout the specification to describe the present invention.

The term "patient" is used throughout the specification to describe a subject animal, preferably a human, to whom treatment, including prophylactic treatment, with the compositions according to the present invention is provided. For treatment of those infections, conditions or disease states which are specific for a specific animal such as a human patient, the term patient refers to that specific animal.

The term "human immunodeficiency virus", "HIV-1" or "HrV" is used to describe the viral causative agent which is responsible for producing HIV infections in human patients, which, if untreated or unresolved will often result in AIDS or related immunological conditions and eventually death in a patient.

The term "dioxolane thymine" is used generically to describe nucleoside compounds according to the present invention which contain both a dioxolane sugar synthon and thymine base, regardless of the R group which is used on the compound. These agents are described stereochemically as β-D nucleoside analogs.

The term "pharmaceutically acceptable salt" is used throughout the specification to describe a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Sodium and potassium salts are particularly preferred as neutralization salts of the phosphates according to the present invention.

The term "pharmaceutically acceptable derivative" is used throughout the specification to describe any pharmaceutically acceptable prodrug form (such as an ester or ether or other prodrug group) which, upon administration to a patient, provides directly or indirectly the present compound or an active metabolite of the present compound.

The term "alkyl" shall mean within its context a $C_1$-$C_{20}$, preferably a $C_1$-$C_{10}$ linear, branch-chained or cyclic fully saturated hydrocarbon radical. The term "ether" shall mean a $C_1$ to $C_{20}$ ether group, formed from an oxygen and an alkyl group, or alternatively, may also contain at least one oxygen within the alkyl or alkylene chain.

The term "acyl" is used throughout the specification to describe a group at the 5' position of the nucleoside analog (i.e., at the free hydroxyl position in the dioxolanyl moiety) which contains a $C_1$ to $C_{20}$ linear, branched or cyclic alkyl chain. The acyl group at the 5' position, in combination with the 5' hydroxyl group results in an ester, which, after administration, may be cleaved to produce the free nucleoside form of the present invention. Acyl groups according to the present invention are represented by the structure:

where $R^4$ is a $C_1$ to $C_{20}$ linear, branched or cyclic alkyl group, alkoxyalkyl (including an ethylene oxide chain which may end in a free hydroxyl group or a $C_1$-$C_{10}$ alkyl group and ranges in molecular weight from about 50 to about 40,000 or about 200 to about 5,000), aryloxyallcyl, such as phenoxymethyl, aryl, alkoxy, among others. Preferred acyl groups are those where $R^4$ is a $C_1$ to $C_{10}$ alkyl group. Acyl groups according to the present invention also include, for example, those acyl groups derived from benzoic acid and related acids, 3-chlorobenzoic acid, succinic, capric and caproic, lauric, myristic, palmitic, stearic and oleic groups, among numerous others including mesylate groups. One of ordinary skill in the art will recognize the acyl groups which will have utility in the present invention, either to synthesize the target pharmaceutical compounds or as prodrug of the nucleosides according to the present invention.

The term "phosphate ester" or "phosphodiester" is used throughout the specification to describe mono-phosphate groups at the 5' position of the dioxanyl moiety or sugar synthon which are diesterified such that the phosphate group is rendered neutral, i.e., has a neutral charge. Phosphate esters for use in the present invention include those represented by the structures:

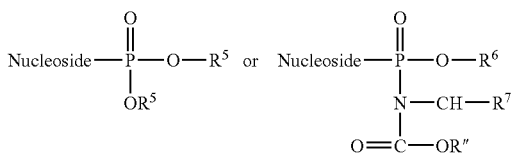

where $R^5$, $R^6$ and $R''$ are selected from a $C_1$ to $C_{20}$ linear, branched or cyclic alkyl group, alkoxyalkyl, aryloxyalkyl, such as phenoxymethyl, aryl and alkoxy, among others, and $R^7$ is a $C_1$ to $C_{20}$ linear, branched or cyclic alkyl or acyl group, alkoxyalkyl, aryloxyalkyl, such as phenoxymethyl, aryl and alkoxy, among others. Preferred monophosphate esters for use in prodrug forms according to the present invention are those where $R^5$ is a $C_1$ to $C_{20}$ linear or branched chain alkyl group, more preferably a $C_1$ to $C_3$ alkyl group.

The term "inhibitory effective concentration" or "inhibitory effective amount" is used throughout the specification to describe concentrations or amounts of compounds according to the present invention which substantially or significantly inhibit the growth or replication of susceptible viruses, especially HIV.

The term "therapeutic effective amount" or "therapeutically effective amount" is used throughout the specification to describe concentrations or amounts of compounds according to the present invention which are therapeutically effective in treating HUV infections in patients.

The term "preventing effective amount" is used throughout the specification to describe concentrations or amounts of compounds according to the present invention which are prophylactically effective in preventing, reducing the likelihood of contracting or delaying the onset of HIV infections or related conditions (such as AIDS) in patients.

The term "effective amount" shall mean an amount or concentration of a compound according to the present invention which is effective within the context of its administration, which may be inhibitory, prophylactic and/or therapeutic. Within context, all active compounds which are used in the present invention are used in effective amounts. The present compound also relates to combinations of compounds which contain effective amounts of each of the compounds used, whether that combination is additive or synergistic in effect, provided that the overall effect of the combination of compounds is to inhibit the growth, reduce the likelihood of or treat HIV infections in patients.

The term "D-configuration" as used in the context of the present invention refers to the configuration of the cyclopentene nucleoside compounds according to the present invention which mimics the natural configuration of sugar moeties of the naturally occurring nucleosides. The term "β" or "β anomer" is used to describe nucleoside analogs according to the present invention in which the nucleoside base (in this case thymine) is configured (disposed) above the plane of the dioxolane moiety in the nucleoside analog.

The term "enantiomerically enriched" is used throughout the specification to describe a nucleoside which includes at least about 95%, preferably at least about 96%, more preferably at least about 97%, even more preferably, at least about 98%, and even more preferably at least about 100% or more of a single enantiomer of that nucleoside. Dioxolane thymine compounds according to the present invention are generally D-nucleoside compounds. When the present dioxolane thymine compounds according to the present invention are referred to in this specification, it is presumed that the nucleosides have the D-nucleoside configuration and are enantiomerically enriched (preferably, about 100% of the D-nucleoside), unless otherwise stated.

The terms "coadminister" and "coadministration" are used synonymously to describe the administration of at least one of the dioxolane thymine nucleoside compounds according to the present invention in combination with at least one other anti-HIV agent, in amounts or at concentrations which would be considered to be effective amounts at or about the same time. While it is preferred that coadministered agents be administered at the same time, agents may be administered at times such that effective concentrations of both (or more) agents appear in the patient at the same time for at least a brief period of time. Alternatively, in certain aspects of the present invention, it may be possible to have each coadministered agent exhibit its inhibitory effect at different times in the patient, with the ultimate result being the inhibition of HIV and the treatment of an HIV infection.

Chemical Synthesis

Compounds according to the present invention may be synthesized by methods known in the art, or alternatively, by the preferred efficient synthetic methods presented in the present specification.

A preferred synthesis which may be used to synthesize compounds according to the present invention is presented in Chu, et al., *Tetrahedron Letters*, vol. 32, No. 31, pp 3791-3794 (1991), which is incorporated by reference herein. Essentially, the present compounds are synthesized in stepwise manner from 1,6-anhydro-D-mannose, which contains the necessary stereochemistry of the enantiomeric dioxolane thymine nucleoside compounds according to the present invention. 1,6-anhydro-D-mannose may be readily converted to a protected dioxolane synthon, which may be prepared for condensation with thymine and condensed with thymine followed by deprotection to afford (−)-(R,R)-dioxolane thymine ($R^1$ is H). $R^1$ groups other than H may be readily inserted at the free hydroxyl position of the dioxolane synthon using readily available techniques which are well-known in the art.

Pharmaceutical compositions based upon the dioxolane thymine nucleoside compounds according to the present invention comprise the above-described compounds in a therapeutically effective amount for treating a viral, especially a HIV infection, optionally in combination with a pharmaceutically acceptable additive, carrier or excipient. One of ordinary skill in the art will recognize that a therapeutically effective amount will vary with the infection or condition to be treated, its severity, the treatment regimen to be employed, the pharmacolcinetics of the agent used, as well as the patient (animal or human) treated.

In the pharmaceutical aspect according to the present invention, the compound according to the present invention is formulated preferably in admixture with a pharmaceutically acceptable carrier. In general, it is preferable to administer the pharmaceutical composition in orally-administrable form, but certain formulations may be administered via a parenteral, intravenous, intramuscular, transdermal, buccal, subcutaneous, suppository or other route. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the routineer's skill to modify the route of administration and dosage regimen of a particular compound in order to manage the pharmacokinetics of the present compounds for maximum beneficial effect in patients.

In certain pharmaceutical dosage forms, the pro-drug form of the compounds, especially including acylated (acetylated or other) and ether (alkyl and related) derivatives, phosphate esters and various salt forms of the present compounds, are preferred. One of ordinary skill in the art will recognize how to readily modify the present compounds to pro-drug forms to facilitate delivery of active compounds to a targeted site within the host organism or patient. The routineer also will take advantage of favorable pharmacolcinetic parameters of the pro-drug forms, where applicable, in delivering the present compounds to a targeted site within the host organism or patient to maximize the intended effect of the compound.

The amount of compound included within therapeutically active formulations according to the present invention is an effective amount for treating the infection or condition, especially 3TC and/or AZT resistant HIV infection. In general, a therapeutically effective amount of the present compound in pharmaceutical dosage form usually ranges from about 0.05 mg/kg to about 100 mg/kg per day or more, more preferably, slightly less than about 1 mg/kg to about 25 mg/kg per day of the patient or considerably more, depending upon the compound used, the condition or infection treated and the route of administration. The active dioxolane thymine nucleoside compound according to the present invention is preferably administered in amounts ranging from about 0.5 mg/kg to about 25 mg/kg per day of the patient, depending upon the pharmacokinetics of the agent in the patient. This dosage range generally produces effective blood level concentrations of active compound which may range from about 0.05 to about 100 micrograms/cc of blood in the patient. For purposes of the present invention, a prophylactically or preventive effective amount of the compositions according to the present invention falls within the same concentration range as set forth above for therapeutically effective amount and is usually the same as a therapeutically effective amount.

Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration. Enteric coated oral tablets may also be used to enhance bioavailability of the compounds from an oral route of administration. The most effective dosage form will depend upon the bioavailability/pharmacokinetics of the particular agent chosen as well as the severity of disease in the patient. Oral dosage forms are particularly preferred, because of ease of admnistration and prospective favorable patient compliance.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques. The use of these dosage forms may significantly the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free nucleosides, acyl/alkyl nucleosides or phosphate ester pro-drug forms of the nucleoside compounds according to the present invention.

In particularly preferred embodiments according to the present invention, the compounds and compositions are used to treat, prevent or delay the onset of an HIV infection. Preferably, to treat, prevent or delay the onset of HIV, the compositions will be administered in oral dosage form in amounts ranging from about 250 micrograms up to about 500 mg or more at least once a day, preferably, up to four times a day. The present compounds are preferably administered orally, but may be administered parenterally, topically or in suppository form.

In the case of the co-administration of the present compounds in combination with another anti-HIV agent, the amount of the dioxolane thymine compound according to the present invention to be administered ranges from about 1 mg/kg of the patient to about 500 mg/kg. or more of the patient or considerably more, depending upon the second anti-HIV agent to be co-administered and its potency against HIV or the strain of HIV to be inhibited, the condition or infection treated and the route of administration. In the case of HIV infections, the other anti-HIV agent may be preferably administered in amounts ranging from about 100 ug/kg (micrograms per kilogram) to about 500 mg/kg. In certain preferred embodiments, these compounds may be preferably administered in an amount ranging from about 1 mg/kg to about 50 mg/kg or more (usually up to about 100 mg/kg), generally depending upon the pharmacokinetics of the agent in the patient. This dosage range generally produces effective blood level concentrations of active compound in the patient. The compounds according to the present invention, may advantageously be employed prophylactically to prevent a viral infection or to prevent the occurrence of clinical symptoms associated with the viral infection. Thus, the present invention also encompasses methods for the prophylactic treatment of an HIV infection. In this aspect according to the present invention, the present compositions are used to prevent, reduce the likelihood of or delay the onset of a HIV or a virus related disease or condition such as AIDS. This prophylactic method comprises administering to a patient in need of such treatment or who is at risk for the development of an HIV infection, an amount of a compound according to the present invention alone or in combination with another anti-HIV agent effective for alleviating, preventing or delaying the onset of the viral infection. In the prophylactic treatment according to the present invention, it is preferred that the antiviral compound utilized should be as low in toxicity and preferably non-toxic to the patient. It is particularly preferred in this aspect of the present invention that the compound which is used should be maximally effective against the virus and should exhibit a minimum of toxicity to the patient. In the case of compounds of the present invention for the prophylactic treatment of viral infections, these compounds may be administered within the same dosage range for therapeutic treatment (i.e., about 250 micrograms up to about 500 mg. or more from one to four times per day for an oral dosage form) as a prophylactic agent to prevent the proliferation of the viral infection or alternatively, to prolong the onset of or reduce the likelihood of a patient contracting a virus infection which manifests itself in clinical symptoms.

In addition, compounds according to the present invention may be administered alone or in combination with other agents, including other compounds of the present invention. Certain compounds according to the present invention may be effective for enhancing the biological activity of certain agents according to the present invention by reducing the metabolism, catabolism or inactivation of other compounds and as such, are co-administered for this intended effect.

The present invention is now described, purely by way of illustration, in the following examples. It will be understood by one of ordinary skill in the art that these examples are in no way limiting and that variations of detail can be made without departing from the spirit and scope of the present invention.

EXAMPLES

Example 1

Evaluation of DOT Against 3TC and/or AZT Resistant Strains of HIV Cell-Based Assays in Human Lymphocytes Cross-Resistance Studies: Human peripheral blood mononuclear (PBM) cells (obtained from Atlanta Red Cross) were isolated by Ficoll-Hypaque discontinuous gradient centrifugation from healthy seronegative donors. Cells were stimulated with phytohemagglutinin A (Difco, Sparks, Md.) for 2-3 days prior to use. M184V, L74V, 4XAZT, K65R, T215Y, T215Y/M184V viruses were obtained from Dr. John Mellor's laboratory (University of Pittsburgh, Pa.). K103N virus was obtained courtesy of prior DuPont Pharmaceuticals. Cross-resistance of beta-D-dioxolane-T (DOT) and other anti-HIV agents was evaluated against the above panel of mutated viruses. DOT was prepared according to the method set forth in Chu, et al., *Tetrahedron Letters*, Vol 32, No. 31, pp. 3791-3794 (1991). Infections were done in bulk for one hour, either with 100 TCID50/1 E7 cells for a flask (T25) assay or with 200 TCID50/6E5 cells/well for a 24 well plate assay. Cells were added to a plate or flask containing a ten-fold serial dilution of the test compound. Assay medium was RPMI-1640 supplemented with heat inactivated 16% fetal bovine serum, 1.6 mM L-glutamine, 80 IU/mil penicillin, 80 µg/ml streptomycin, 0.0008% DEAE-Dextran, 0.045% sodium bicarbonate, and 26 IU/ml recombinant interleukin-2 (Chiron Corp, Emeryville, Calif.). Untreated and uninfected PBM cells were grown in parallel at equivalent cell concentrations as controls. The cell cultures were maintained in a humidified 5% $CO_2$-air at 37° C. for 5 days and supernatants were collected for reverse transcriptase (RT) activity.

Supernatants were centrifuged at 12,000 rpm for 2 hr to pellet the virus. The pellet was solubilized with vortexing in 100 µl virus solubilization buffer containing 0.5% Triton X-100, 0.8 M NaCl, 0.5 mM phenylmethylsulfonyl fluoride, 20% glycerol, and 0.05 M Tris, pH 7.8. Ten microliters of each sample were added to 75 microliters reverse transcriptase (RT) reaction mixture (0.06 M Tris, pH 7.8, 0.012 M MgCl2, 0.006 M dithiothreitol, 0.006 mg/ml poly (rA)n oligo (dT)12-18, 96 microg/ml dATP, and 1 µM of 0.08 mCi/ml $^3$H-thymidine triphosphate (Moravek Biochemicals, Brea, Calif.) and incubated at 37° C. for 2 hr. The reaction was stopped by the addition of 100 µl 10% trichloroacetic acid (TCA) containing 0.05% sodium pyrophosphate. The acid insoluble product was harvested onto filter paper using a Packard Harvester (Meriden, Conn.), and the RT activity was read on a Packard Direct Beta Counter (Meriden, Conn.). The RT results were expressed in counts per minute (CPM) per milliliter. The antiviral 50% effective concentration (EC50) and 90% effective concentration (EC90) were determined from the concentration-response curve using the median effect method of Belen'kii and Schinazi. Multiple drug effect analysis with confidence interval. *Antivir. Res.* 25:1-11 (1994). Table 1, below provides data related to the above-described experiments and the effects of DOT on AZT and/or 3TC resistant HIV strains.

TABLE 1

Activity of Dioxolane Thymine Against Drug Resistant HIV

| Virus | $EC_{50}$ μM | $EC_{90}$ μM | SLOPE | R | $FI_{50}$ Fold Increase In $EC_{50}$ | $FI_{90}$ Fold Increase In $EC_{90}$ |
|---|---|---|---|---|---|---|
| XXBRU (1) | 0.38 | 3.0 | 1.1 ± 0.13 | 0.98 | | |
| XXBRU (2) | 0.48 | 6.7 | 0.83 ± 0.11 | 0.98 | | |
| Avg. | 0.43 | 4.9 | | | | |
| St. Dev. | 0.07 | 2.6 | | | | |
| $K65R_{PITT}$(1) | 0.99 | 6.3 | 1.1 ± 0.12 | 0.98 | 0.83 | 0.86 |
| $K65R_{PITT}$(2) | 0.21 | 3.1 | 0.82 ± 0.16 | 0.96 | 0.28 | 0.60 |
| Avg. | 0.60 | 4.7 | | | 0.55 | 0.73 |
| St. Dev. | 0.55 | 2.3 | | | 0.39 | 0.19 |
| XXBRU (1) | 1.2 | 7.3 | 1.2 ± 0.16 | 0.98 | | |
| XXBRU (2) | 0.76 | 5.2 | 1.1 ± 0.13 | 0.99 | | |
| Avg. | 0.98 | 6.3 | | | | |
| St. Dev. | 0.31 | 1.5 | | | | |
| 4X $AZT_{PITT}$ | 0.49 | 8.4 | 0.77 ± 0.003 | 0.99 | 2.0 | 3.8 |
| XXBRU | 0.24 | 2.2 | 1.0 ± 0.02 | 0.99 | | |
| $L74V_{PITT}$ | 0.33 | 2.3 | 1.1 ± 0.29 | 0.96 | 0.75 | 0.49 |
| XXBRU | 0.44 | 4.7 | 0.93 ± 0.06 | 0.99 | | |
| K103N | 1.4 | 5.4 | 1.6 ± 0.19 | 0.99 | 14.0 | 2.6 |
| XXBRU | 0.10 | 2.1 | 0.74 ± 0.12 | 0.97 | | |
| T215Y | 0.27 | 5.9 | 0.71 ± 0.13 | 0.98 | 2.7 | 5.9 |
| XXBRU | 0.10 | 1.0 | 0.95 ± 0.19 | 0.98 | | |
| T215Y/M184V | 0.32 | 2.4 | 1.1 ± 0.14 | 0.99 | 0.46 | 0.92 |
| XXBRU | 0.69 | 2.6 | 1.7 ± 0.18 | 0.99 | | |

Example 2

In related experiments, dioxolane thymine (DOT), beta-D-9-(5-hydroxymethyl-dioxolanyl-2-yl)-2,4-diamino-purine (DAPD) and beta-D-9-(5-hydroxymethyl-dioxolanyl-2-yl) guanine (DXG) were evaluated for their inhibitory effects against a number of 3TC and/or AZT resistant strains of HIV. The following Tables 2 and 3, set forth below, describe the HIV resistant strains genotypically (Table 2) and phenotypically (Table 3) which were used in the experiments to test activity.

TABLE 2

Genotype of HIV-1 Sensitive/Resistant Matched Pairs

| Pre-treatment Isolate (background) | Post-treatment Isolate (resistant) | Mutations in Reverse Transcriptase Gene of Post-treatment Isolate |
|---|---|---|
| 5705-0 | 5705-72 | D67N, K70R, K103N, I135L, M184V, K219E, R284K, C355F, R356K |
| 488-0 | 488-101 | M41L, E122K, M184V, T215Y |
| H112-2 | C910-6 | M41L, D67N, K70R, T215Y, K219Q (other mutations not associated with AZT/R = V60I, K83R, H208Y, L239V, R356K and G359S) |
| LAI | LAI M184V | M184V |

TABLE 3

Phenotype of HIV-1 Sensitive/Resistant Matched Pairs

| Virus Isolate | Drug ($IC_{50}$) AZT | 3TC | AZT Phenotype | 3TC Phenotype |
|---|---|---|---|---|
| 5705-0 | 3-8 nM | 4-9 nM | Sensitive | Sensitive |
| 5705-72 | 30 nM | >50 μM | Low-level Resistance | Highly Resistant |
| 488-0 | 0.3-0.6 nM | 30-47 nM | Sensitive | Sensitive |
| 488-101 | 80 nM | 40.6 μM | Resistant | Highly Resistant |
| LAI | 20 nM | 10 nM | Sensitive | Sensitive |
| LAI-M184V | 10 nM | >50 μM | Sensitive | Highly Resistant |
| H112-2 | 10 nM | 170 nM | Sensitive | Sensitive |
| G910-6 | 620 nM | 320 nM | Resistant | Sensitive |

Each of the three test compounds were tested for efficacy against the various strains of HIV-1. Anti-HIV efficacy was evaluated in PBMC, reverse transcriptase activity was tested in a microtiter plate-based reverse transcriptase assay (Buckeit, et al., *AIDS Research and Human* Retroviruses, 7:295-302, 1991), MTS staining was used for determining cell viability. $EC_{50}$ (50% effective inhibition of virus replication), $TC_{50}$ (50% cytotoxicity) and therapeutic index (TI, $TC_{50}$/$IC_{50}$) were determined for each of the compounds on each of the resistant viral strains described above. The results for Dioxolane Thymine are presented in Table 4, below. Table 5 presents a resistance phenotype comparison for compounds of the present invention versus the compounds 3TC and AZT.

TABLE 4

Antiviral Efficacy of DOT in Resistant Strains in PBMC's

| Resistant Strain | $EC_{50}$ | $TC_{50}$ | Therapeutic Index | Activity |
|---|---|---|---|---|
| 5705-02 | 2.44 μg/ml | >100 μg/ml | >41 | Active[1] |
| 488-101 | 1.13 μg/ml | >100 μg/ml | >42 | Active[2] |

TABLE 4-continued

Antiviral Efficacy of DOT in Resistant Strains in PBMC's

| Resistant Strain | $EC_{50}$ | $TC_{50}$ | Therapeutic Index | Activity |
|---|---|---|---|---|
| G910-6 | 0.29 µg/ml | >100 µg/ml | >345 | Highly Active[3] |
| LAI M184V | 0.29 µg/ml | >40 µg/ml | >137 | Highly Active[4] |

[1]Viral Strains were found to be highly resistant* and resistant* to 3TC and AZT, respectively.
[2]Viral Strains were found to be resistant* to 3TC and AZT, respectively.
[3]Viral Strains were found to be sensitive* and resistant* to 3TC and AZT, respectively.
[4]Viral Strains were found to be high resistant* and sensitive* to 3TC and AZT, respectively.
*Sensitivity Profile - <5 fold resistance, Sensitive; >5 fold resistance, Resistant; >100 fold resistance, Highly Resistant.

TABLE 5

Resistance Phenotype Comparison

| Compound | Phenotype for 5705-02[1] | Phenotype for 488-101[1] | Phenotype for G910-6[1] | Phenotype for LAI M184V[1] |
|---|---|---|---|---|
| DAPD | Resistant | Sensitive | Sensitive | Sensitive |
| DXG | Highly Resistant | Sensitive | Sensitive | Resistant |
| DOT | Sensitive | Sensitive | Sensitive | Sensitive |
| 3TC | Highly Resistant | Resistant | Sensitive | Highly Resistant |
| AZT | Sightly Resistant | Highly Resistant | Resistant | Sensitive |

[1]Sensitivity Profile- <5 fold resistance, Sensitive; >5 fold resistance, Resistant; >100 fold resistance, Highly Resistant.

Discussion

DAPD, DXG and DOT were evaluated for antiviral efficacy against a panel of HIV-1 3TC/AZT drug sensitive/resistant matched pair virus isolates in a standardized PBMC cell-based anti-HIV assay. The compounds were also evaluated in a parallel assay for cytotoxicity in uninfected PBM cells.

All compounds proved to be active to highly active against the four AZT/3TC sensitive HIV-1 isolates. However, in comparison to the AZT and/or 3TC resistant viruses, the following observations are apparent.

1. None of the AZT/3TC resistant isolates was cross-resistant to DOT malting this compound an excellent candidate for the treatment of AZT and/or 3TC resistant HIV strains.

2. DXG exhibited a resistance profile similar to that of 3TC, however, the overall degree of resistance is generally less than for 3TC.

3. DAPD exhibited a resistance profile similar to AZT, although not all AZT resistant isolates were cross-resistant to this compound.

It is to be understood by those skilled in the art that the foregoing description and examples are illustrative of practicing the present invention, but are in no way limiting. Variations of the detail presented herein may be made without departing from the spirit and scope of the present invention as defined by the following claims.

The invention claimed is:

1. A method of treating a drug resistant HIV infection in a patient, comprising administering to a patient in need of therapy an effective amount of a dioxolane thymine compound according to the chemical structure:

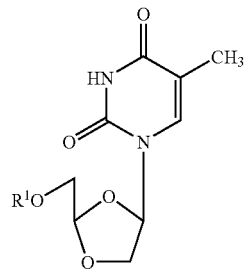

where $R^1$ is H, an acyl group, a $C_1$-$C_{20}$ alkyl or ether group, a phosphate, diphosphate, triphosphate or phosphodiester group, or a pharmaceutically acceptable salt thereof in combination with at least one anti-HIV agent which inhibits HLV by a mechanism other than through inhibition of viral thymidine kinase, wherein said HIV infection is caused by a drug resistant strain of HIV selected from the group consisting of K65R, M184V and T215Y.

2. The method according to claim 1, wherein said dioxolane thymine compound is coadministered with at least one anti-HIV agent selected from the group consisting of nucleoside reverse transcriptase inhibitors, non-nucleoside reverse transcriptase inhibitors, protease inhibitors and fusion inhibitors.

3. The method according to claim 1, wherein said dioxolane thymine compound is coadministered with at least one anti-HIV agent selected from the group consisting of 3TC, (Lamivudine) (−)-FTC, (emtricitabine) ddI, (didanosine) ddC, (Zalcitabine) abacavir, tenofovir, D-D4FC, (reverset) racivir, L-D4FC, (L-beta-2',3'-didehydro-2',3'-dideoxy-5-fluorocytidine) NVP, (Nevirapine) DLV, (Delaviridine) EFV, (Efivirenz) SQVM, (Sapuanivir mesvlate) RTV, (Ritanovir) IDV, (indinavir) SQV, (Sapuinavir) NFV, (Nelfinavir) APV, (amprenavir) LPV, (lopinavir) fuseon and mixtures thereof.

4. The method according to claim 1, wherein $R^1$ is H or a $C_2$-$C_{18}$ acyl group.

5. The method according to claim 1, wherein $R^1$ is H.

6. The method according to claim 2, wherein $R^1$ is H.

7. The method according to claim 3, wherein $R^1$ is H.

8. The method according to claim 4, wherein $R^1$ is a $C_2$-$C_{18}$ acyl group.

9. A method of reducing the likelihood that a patient will be infected with drug resistant HIV, said method comprising administering to a patient at risk for developing HIV an effective amount of a dioxolane thymine compound according to the chemical structure:

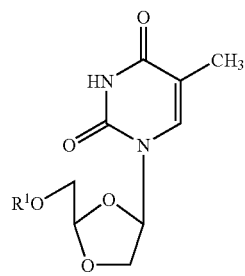

where $R^1$ is H, an acyl group, a $C_1$-$C_{20}$ alkyl or ether group, a phosphate, diphosphate, triphosphate or phosphodiester group, or a pharmaceutically acceptable salt thereof, optionally in combination with at least one anti-HIV agent which inhibits HIV by a mechanism other than through inhibition of viral thymidine kinase, wherein said HIV infection is caused by a drug resistant strain of HIV selected from the group consisting of K65R, M184V and T215Y.

10. The method according to claim 9, wherein said dioxolane thymine compound is coadministered with at least one anti-HIV agent selected from the group consisting of nucleoside reverse transcriptase inhibitors, non-nucloeoside reverse transcriptase inhibitors, protease inhibitors and fusion inhibitors.

11. The method according to claim 9, wherein said dioxolane thymine compound is coadministered with at least one anti-HIV agent selected from the group consisting of 3TC, (Lamivudine) (−)-FTC, (emtricitabine) ddI, (didanosine) ddC, (Zalcitabine) abacavir, tenofovir, D-D4FC, (reverset) racivir, L-D4FC, (L-beta-2',3'-didehydro-2',3'-dideoxy-5-fluorocytidine) NVP, (Nevirapine) DLV, (Delaviridine) EFV, (Efivirenz) SQVM, (Saquanivir mesylate) RTV, (Ritanovir) IDV, (indinavir) SQV, (Saquinavir) NFV, (Nelfinavir) APV, (amprenavir) LPV, (Iopinavir) fuseon and mixtures thereof.

12. The method according to claim 9, wherein $R^1$ is H or a $C_2$-$C_{18}$ acyl group.

13. The method according to claim 9, wherein $R^1$ is H.

14. The method according to claim 10, wherein $R^1$ is H.

15. The method according to claim 11, wherein $R^1$ is H.

16. The method according to claim 12, wherein $R^1$ is a $C_2$-$C_{18}$ acyl group.

* * * * *